United States Patent
Wessig et al.

(10) Patent No.: US 7,423,117 B2
(45) Date of Patent: *Sep. 9, 2008

(54) SURFACE-FUNCTIONALIZED CARRIER MATERIAL AND SOLID PHASE SYNTHESIS METHOD

(75) Inventors: Pablo Wessig, Berlin (DE); Jürgen Bendig, Berlin (DE); Uwe Schedler, Berlin (DE)

(73) Assignee: Ploy-An Gesellschaft zur Herstellung von Polymeren Fuer Spezielle Anwendungen und Analytik mbH, Berlin (DE)

( * ) Notice: Subject to any disclaimer, the term of this patent is extended or adjusted under 35 U.S.C. 154(b) by 295 days.

This patent is subject to a terminal disclaimer.

(21) Appl. No.: 10/451,654

(22) PCT Filed: Dec. 3, 2001

(86) PCT No.: PCT/EP01/14073

§ 371 (c)(1),
(2), (4) Date: Jan. 22, 2004

(87) PCT Pub. No.: WO02/051917

PCT Pub. Date: Jul. 4, 2002

(65) Prior Publication Data

US 2005/0003501 A1 Jan. 6, 2005

(30) Foreign Application Priority Data

Dec. 22, 2000 (DE) ................. 100 65 788

(51) Int. Cl.
- *C07K 1/04* (2006.01)
- *C07K 1/06* (2006.01)
- *C07K 1/10* (2006.01)
- *C12K 17/06* (2006.01)
- *C12N 11/06* (2006.01)
- *G01N 33/547* (2006.01)

(52) U.S. Cl. .............. 530/334; 435/181; 436/532; 530/335; 530/337; 530/402; 530/816

(58) Field of Classification Search ............... None
See application file for complete search history.

(56) References Cited

U.S. PATENT DOCUMENTS 5,389,533 A 2/1995 von Gentzkow et al. .... 435/180

OTHER PUBLICATIONS

Dörwald, 'Organic Synthesis on Solid Phase,' p. 414-47, Wiley Publish. Co. Chemistry, Weinheim, Germany (2000).
Arshady et al., 'Peptide Synthesis. Part 1. Preparation and Use of Polar Supports based on Poly(dimethylacrylamide),' J. Chem. Soc. Perkin Trans. I, 529-37 (1981).
Matsueda et al., 'Solid Phase Peptide Synthesis by Oxidation-Reduction Condensation,' J. Am. Chem. Soc., 97:2573-5 (1975).
Carpino et al., 'The 9-Fluorenylmethoxycarbonyl Amino-Protecting Group,' J. Org. Chem., 37(22):3404-9 (1972).
Letsinger et al., 'Popcorn polymer as a Support in Multistep Syntheses,' J. Am. Chem. Soc., 85:304506 (1963).
Merrifield, 'Solid Phase Peptide Synthesis. I. The Synthesis of a Tetrapeptide,' J. Am. Chem. Soc., 85:2149-54 (1963).

*Primary Examiner*—David M Naff
(74) *Attorney, Agent, or Firm*—Kriegsman & Kriegsman

(57) ABSTRACT

The invention concerns a novel surface-functionalized carrier material with a polymeric surface and at least one linker compound according to the general formula (I), which is covalently bound to the surface. In the formula, P indicates the polymeric surface; $R^2$ has the meaning $OR^4$ or $NR^4R^5$ and $R^1$, $R^4$ and $R^5$, independently of one another, indicate H, an alkyl group or an aryl group; $R^3$ indicates H, an alkyl, an aryl, an acyl, an alkoxycarbonyl or an aryloxycarbonyl group; and the alkyl, aryl, acyl, alkoxycarbonyl and/or aryloxycarbonyl group of the radicals $R^1$, $R^3$, $R^4$ and $R^5$, independently of one another, are substituted or unsubstituted. The material according to the invention can be very easily produced by photochemical coupling and serves for the solid-phase synthesis of amino acids, peptides, proteins or molecules with at least one peptidic structural unit.

16 Claims, 2 Drawing Sheets

SURFACE-FUNCTIONALIZED CARRIER MATERIAL AND SOLID PHASE SYNTHESIS METHOD

BACKGROUND OF THE INVENTION

1. Field of the Invention

The invention concerns a surface-functionalized carrier material comprising a carrier material and at least one linker compound covalently bound to a polymeric surface of the latter, a method for the production thereof as well as a method for the solid-phase synthesis of amino acids, peptides or molecules with at least one peptide structural unit.

2. Description of Related Art

Conducting the synthesis of peptides or more complex molecules with peptide structural units in the form of so-called solid-phase syntheses is known. For this purpose, an amino acid which represents virtually the first molecular member of the peptide sequence to be produced is covalently bound to a carrier material that is not soluble in water and whose surface bears suitable functional groups. Further extension of the chain is produced by successively binding additional amino acids, which correspond to the sequence to be constructed, to the first amino acid or to the free end of the forming peptide chain. In addition to pure chain extension, the conducting of chemical modifications at the immobilized amino acid or the immobilized peptide is also known. Polystyrene is primarily used as the basic material for the solid phase (the carrier material) (refer to: F. Z. Dörwald, Organic Synthesis on Solid Phases, Wiley Publishing Co. Chemistry, Weinheim 2000, pp. 414 ff).

Two strategies are distinguished with respect to the direction of synthesis of the peptide to be produced. In the Merrifield strategy, which is also denoted as type A extension, a surface functionalization of the polystyrene is conducted by derivatizing with chloromethyl, hydroxymethyl or acrylamide groups (R. B. Merrifield, J. Am. Chem. Soc. 1963, 85, pp. 2149-2154; R. Arshady et al., J. Chem. Soc. Perkin Trans. I 1981, pp. 529-537). The covalent coupling of the first amino acid to these groups is conducted via the carboxyl group of the amino acid, i.e., the C terminal. The further construction of the chain includes a condensation of the subsequent amino acid to the amino group (the N terminal) of the already immobilized amino acid, or—in further synthesis—the immobilized peptide. According to the Merrifield strategy, synthesis is produced accordingly from the C terminal to the N terminal of the peptide. Also, in the Boc strategy derived from the Merrifield concept (R. Arshady et al., J. Chem. Soc. Perkin Trans I 1981, 529-537) or the Fmoc strategy (L. A. Carpino, G. Y. Han, J. Org. Chem. 1972, 37, 3404-3409), in which the amino group of the respective amino acids to be coupled is protected by specific protective groups, the peptide is finally bound to the solid phase via the carbonyl function of the first amino acid.

In contrast, in the inverse strategy (type B extension), chloroformic acid ester units immobilized on the surface of polystyrene are used as the starting point for the peptide synthesis (R. L. Letsinger, M. J. Kornet, J. Am. Chem. Soc. 1963, 85, 2149-2154; R. Matsueda et al., J. Am. Chem. Soc. 1975, 97, 2573-2575). The synthesis is conducted here by N-terminal coupling of the amino acids protected as tert-butyl esters in the sequence given in advance by the target sequence in the direction of the C terminal of the peptide.

It is a disadvantage in this prior art that, independent of the desired synthesis strategy, carrier materials with different functionalizations must be utilized, since the chemical properties of the respective surface function of the carrier material permit exclusively an N terminal or a C terminal coupling of the amino acid.

SUMMARY OF THE INVENTION

The object of the present invention is thus to provide a surface-functionalized carrier material, which permits a user selectively a C terminal or an N terminal binding of an amino acid or another molecule with appropriate functional groups. A method for the production of surface-functionalized carrier material as well as a method for solid-phase synthesis will also be provided.

The first aspect of this object is solved by a surface-functionalized carrier material with a polymeric surface and at least one linker compound according to general formula (I), which is covalently bound to the surface:

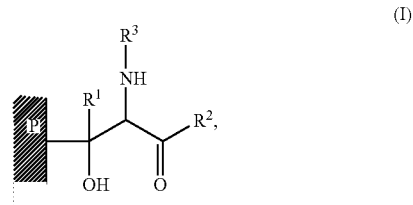

(I)

in which P indicates the polymeric surface; $R^2$ has the meaning $OR^4$ or $NR^4R^5$ and $R^1$, $R^4$ and $R^5$, independently of one another, indicate H, an alkyl group or an aryl group; $R^3$ indicates H, an alkyl, an aryl, an acyl, an alkoxycarbonyl or an aryloxycarbonyl group; and the alkyl, aryl, acyl, alkoxycarbonyl and/or aryloxycarbonyl group of the radicals $R^1$, $R^3$, $R^4$ and $R^5$, independently of one another, are substituted or unsubstituted. The linker compound covalently bound to the carrier material can be based on the amino acid glycine, whose amino and/or carboxyl group is optionally derivatized and which is covalently bound at its $C^\alpha$ position via a hydroxyethyl unit to the polymeric surface of the carrier material. The hydroxyethyl unit at the C position bearing the hydroxy group may also be substituted. The material according to the invention is accordingly characterized in that it bears two free functions, i.e., the amino and the carboxyl groups of the glycine, at which a biomolecule, particularly an amino acid, can be condensed. The material according to the invention thus involves a doubly surface-functionalized material.

The alkyl groups of the radicals $R^1$, $R^3$, $R^4$ and $R^5$ as well as the alkyl residues of the acyl or the alkoxycarbonyl group of the radical $R^3$ are preferably branched or unbranched, saturated or unsaturated C1 to C20 units. Advantageously, phenyl groups can be utilized as the aryl groups of the radicals $R^1$, $R^3$, $R^4$ and $R^5$ as well as the aryl residue of the aryloxycarbonyl group of the radical $R^3$.

The polymeric surface and/or the carrier material itself is an organic polymer according to an advantageous embodiment, particularly polypropylene, polyethylene, polysulfone, polyether sulfone, polystyrene, polyvinyl chloride, polyacrylonitrile, cellulose, amylose, agarose, polyamide, polyimide, polytetrafluoroethylene, polyvinylidene difluoride, polyester, polycarbonate, polyacrylate, polyacrylamide or a derivative of these or a copolymer or a blend thereof. In addition, however, inorganic and/or mineral materials can also be utilized as carrier materials, particularly glasses, silicates, ceramic materials or metals. It is also conceivable to use composites of one or more inorganic and/or mineral materials and one or more organic polymers. In the case of pure inorganic and/or mineral carrier materials, a coating with one of the named organic polymer materials may be necessary in order to make possible a binding of the linker compound.

With respect to its external configuration, the carrier material can be present in the form of a membrane, a film, a plate, a microtiter plate, a test tube, a glass slide, a fiber, a hollow fiber, a nonwoven material, a woven fabric, a powder, a granulate or in the form of particles. Thus, the carrier material may have a porous or nonporous structure each time. It is most preferably provided that the carrier material is present in the form of a membrane with a symmetrical or asymmetrical pore structure, whereby a pore size can lie in the range of 1 nm to 10 μm.

The surface-bifunctionalized polymer material is produced preferably by:

a) Introducing a linker compound according to general formula II

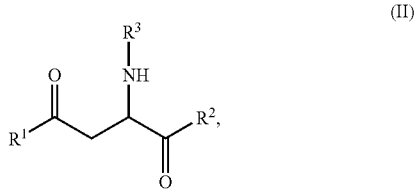

in which $R^1$, $R^2$ and $R^3$ have the above meaning, onto a polymeric surface (P) of a carrier material, and b) Irradiating the surface with light of the UV-vis spectral region, whereby a covalent bond forms between the compound according to formula (II) and the polymeric surface (P) with the formation of the surface-functionalized carrier material according to formula (I).

The glycine derivative according to formula (II) is introduced onto the carrier material or its polymeric surface, which is selected from the above-described materials, by impregnating, moistening or coating, depending on the external shape of the carrier material.

The surface can be exposed—although this is not absolutely necessary—particularly advantageously in the presence of a sensitizer. The yield of the photoreaction can be increased in this way. Irradiation is preferably conducted with light of the wavelength region of 250 to 500 nm. The selection of the wavelength or the wavelength region used primarily depends on the radical $R^1$, the polymeric surface and the presence of and the type of sensitizer. Suitable light sources are, for example, lasers, UV tubes or mercury vapor lamps, whereby the wavelength region can be limited optionally by the use of suitable filters. The light-induced coupling of molecules to polymeric surfaces is known, for example, from WO 91/16425 or EP 0 562,373 A2, and will not be explained in further detail here.

After the photochemical conversion has been produced, unreacted linker compound, by-products and, optionally, the sensitizer can be removed by washing with water, an organic solvent or a solvent mixture, and the functionalized carrier material is dried. The dried product has a very good stability and can be stored at room temperature for weeks and months.

The surface-functionalized carrier material according to the invention can be used for the covalent immobilization of biomolecules, particularly of amino acids, peptides or proteins or other molecules with amino and/or carboxyl groups.

It can also be utilized particularly advantageously for the solid-phase synthesis of amino acids, peptides, proteins or molecules with at least one peptide structural unit. Thus, a first amino acid utilized for the synthesis can be bound to the carrier material by a peptide bond, selectively, either between the amino group of the amino acid and the C1 position of the linker compound or between the carboxyl group of the amino acid and the amino group of the linker compound. If a selective C- or N-terminal bond is desired, the coupling can be controlled in the known way by use of chemical protective groups for blocking the N terminal or the C terminal of the amino acid and/or the C1 position or the amino group of the linker compound. Thus, the terminal of the amino acid which is not to be bound or the function of the linker compound that is not to be connected is blocked by the protective group. Relative to the linker compound, the coupling of the biomolecule can be controlled by suitable selection of the radicals $R^2$ or $R^3$.

The region-specific immobilization of an amino acid is shown in FIG. 3, wherein the radicals $R^1$ and $R^3$ of the surface-immobilized linker compound (a) are each hydrogens and the radical $R^2$ is a hydroxyl group. According to the upper branch of Figure (b), the first amino acid, whose amino function is protected with a tert-butoxycarbonyl protective group (Boc), is condensed by its free carboxyl function at the amino group of the carrier material, with the formation of an amide bond. The carboxyl group can be activated beforehand by reacting the amino acid with dicyclohexylcarbodiimide (DCCl). This measure is also known to the person skilled in the art. The peptide chain of the covalently coupled amino acid can now be extended in such a way that after acidic hydrolytic removal of the Boc protective group, additional amino acids that are protected at the N terminal can be condensed at the now free N terminal of the first amino acid (type A extension). The individual method steps of coupling and cleavage of the protective groups are repeated until the desired peptide sequence is completely constructed. The finished peptide is cleaved by addition of dilute hydrofluoric acid.

The inverse strategy (type B extension) proceeds according to the lower branch (C) of FIG. 3. Here, the carboxyl group of the amino acid to be immobilized is protected by a tert-butyl ester. Consequently, the amino acid can be condensed with the surface-functionalized carrier material only via the amino group of the amino acid to the carboxyl group of the carrier material. For further peptide construction, the tert-butyl group is first removed by saponification, and then other amino acids, which are appropriately protected, are added by condensation.

DETAILED DESCRIPTION OF THE INVENTION

The invention will be explained in further detail below in examples of embodiment.

EXAMPLE 1

Figure 2:
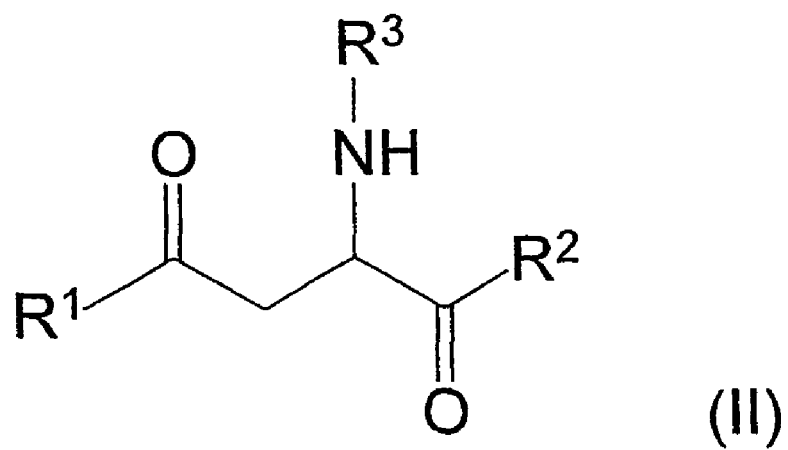
FIG. 2 shows a linker compound used for functionalizing a polymeric surface of a carrier material.
Figure 3:
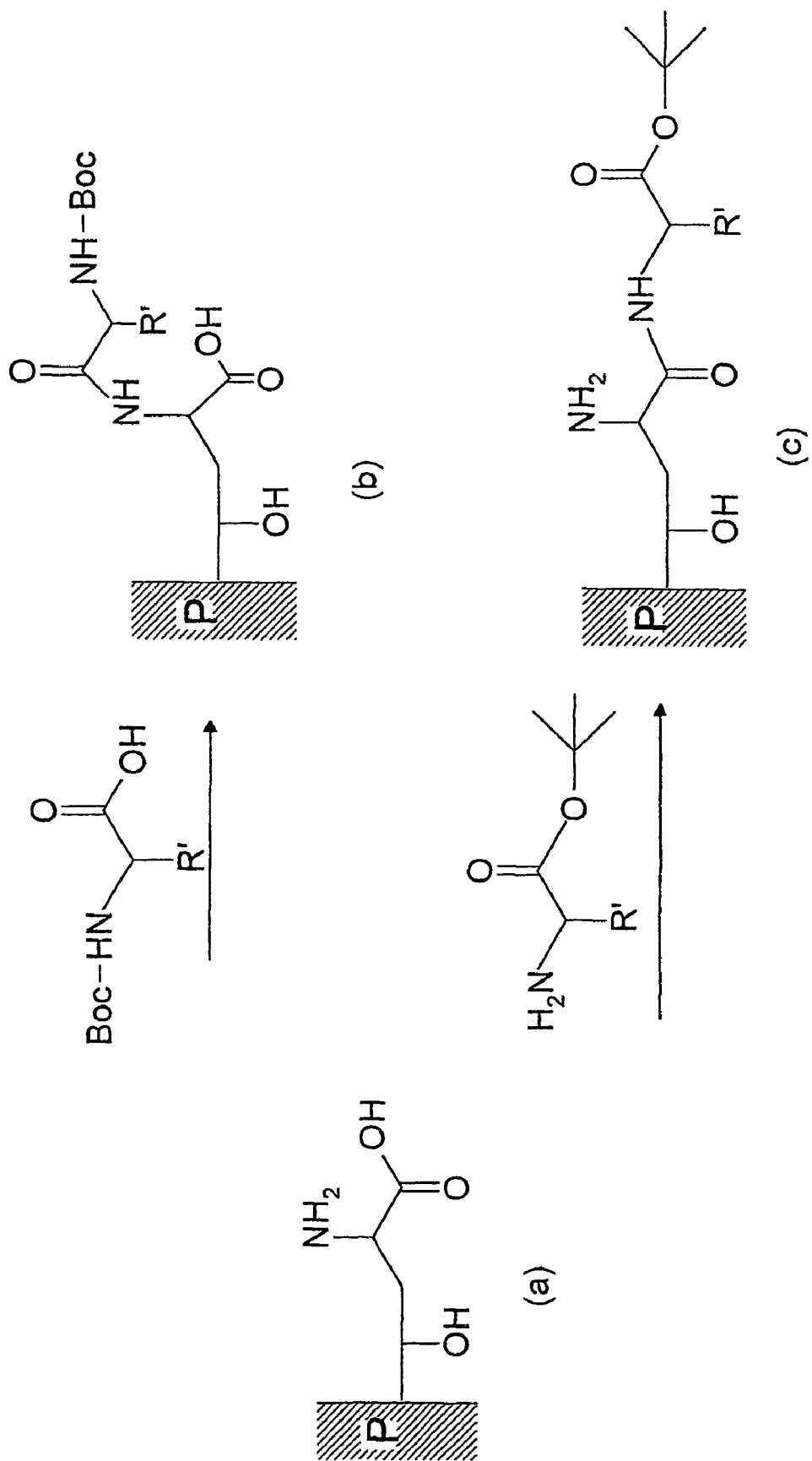
FIG. 3 shows an overview of the steps of a method for immobilizing a biomolecule onto a functionalized carrier material according to the present invention.

A polypropylene membrane (diameter 30 mm) was immersed for 30 minutes in a 0.1 M solution of N-Boc-L-β-benzoylalanine, i.e., an amino acid of the general formula (II) (compare FIG. 2) with $R^1$=phenyl, $R^2$=$OR^4$, $R^3$=t-butoxycarbonyl (Boc) and $R^4$=H, in dichloromethane, and then dried in high vacuum at $3 \cdot 10^{-5}$ Torr for 30 minutes.

The membrane was irradiated for 30 minutes with the light of an HBO (maximum-pressure light) 500 at a distance of 20 cm with the use of a cutoff filter, which filters out light below 290 nm.

The membrane was then washed five times with a total of 150 ml of dichloromethane and dried for 30 minutes in high vacuum at $3 \cdot 10^{-5}$ Torr.

Figure 1:
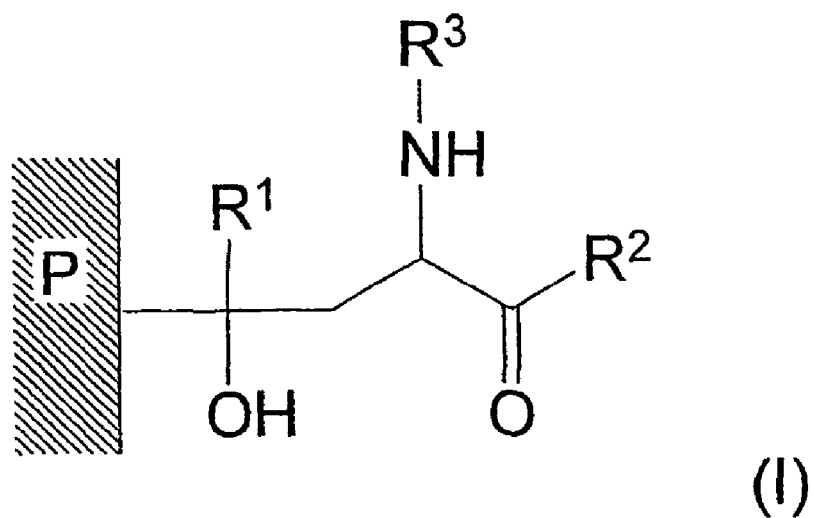
FIG. 1 shows a structure of a carrier material according to the present invention which is functionalized with a linker compound.

The the surface functionalization according to formula (I) (compare FIG. 1), in which $R^1$ to $R^4$ have the above-named meanings, was detected by comparison of the FT-IR spectra for the polypropylene membrane before and after treatment.

EXAMPLE 2

A polypropylene membrane (diameter 30 mm) was immersed for 30 minutes in a 0.1 M solution of N-Boc-L-P-benzoylalanine methyl ester, i.e., an amino acid of the general formula (II) with $R^1$=phenyl, $R^2$=$OR^4$, $R^3$=t-butoxycarbonyl (Boc) and $R^4$=methyl, in dichloromethane, and then dried in high vacuum at $3 \cdot 10^{-5}$ Torr for 30 minutes.

The membrane was irradiated for 30 minutes with the light of an HBO 500 at a distance of 20 cm with the use of a cutoff filter, which filters out light below 290 nm.

The membrane was then washed five times with a total of 150 ml of dichloromethane and dried for 30 minutes in high vacuum at $3 \cdot 10^{-5}$ Torr.

The surface functionalization according to formula (I), in which $R^1$ to $R^4$ have the above-named meanings, was detected by comparison of the FT-IR spectra for the polypropylene membrane before and after treatment.

EXAMPLE 3

A polypropylene membrane (diameter 30 mm) was irradiated in a glass dish, filled with a 0.1 M solution of N-Boc-L-β-benzoylalanine, i.e., an amino acid of the general formula (II) with $R^1$=phenyl, $R^2$=$OR^4$, $R^3$=t-butoxycarbonyl (Boc) and $R^4$=H, in benzene for 60 minutes with the light of an HBO 500 at a distance of 20 cm with the use of a tilted mirror and a cutoff filter, which filters out light below 290 nm.

The membrane was then washed once with 50 ml of benzene and twice with 50 ml of dichloromethane and dried for 30 minutes in high vacuum at $3 \cdot 10^{-5}$ Torr.

The surface functionalization according to formula (I), in which $R^1$ to $R^4$ have the above-named meanings, was detected by comparison of the FT-IR spectra for the polypropylene membrane before and after treatment.

The invention claimed is:

1. A surface-functionalized carrier material with a polymeric surface and at least one linker compound covalently bound to the polymeric surface, wherein said surface-functionalized carrier material has the general formula (I):

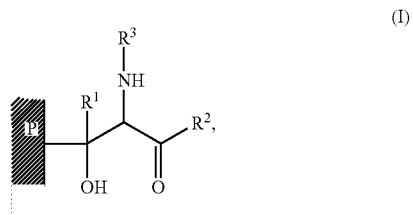

in which P indicates the polymeric surface; $R^2$ of the linker compound has the meaning $OR^4$ or $NR^4R^5$ and $R^1$, $R^4$ and $R^5$ of the linker compound, independently of one another, indicate H, an alkyl group or an aryl group; $R^3$ of the linker compound indicates H, an alkyl, an aryl, an acyl, an alkoxycarbonyl or an aryloxycarbonyl group; and the alkyl, aryl, acyl, alkoxycarbonyl and/or aryloxycarbonyl group of $R^1$, $R^3$, $R^4$ and $R^5$, independently of one another, are substituted or unsubstituted.

2. The surface-functionalized carrier material according to claim 1, wherein the polymeric surface (P) is an organic polymer.

3. The surface-functionalized carrier material according to claim 2, wherein the organic polymer is polypropylene, polyethylene, polysulfone, polyether sulfone, polystyrene, polyvinyl chloride, polyacrylonitrile, cellulose, amylose, agarose, polyamide, polyimide, polytetrafluoroethylene, polyvinylidene difluoride, polyester, polycarbonate, polyacrylate, polyacrylamide or a derivative of these or a copolymer or a blend thereof.

4. The surface-functionalized carrier material according to claim 1, wherein the carrier material is an inorganic and/or mineral material.

5. The surface-functionalized carrier material according to claim 4, wherein the carrier material is a glass, a silicate, a ceramic material or a metal.

6. The surface-functionalized carrier material according to one of claims 2 to 5, wherein the carrier material is a composite of at least one inorganic and/or mineral material and at least one organic polymer.

7. The surface-functionalized carrier material according to claim 1, wherein the carrier material is present in the form of a membrane, a film, a plate, a microtiter plate, a test tube, a glass slide, a fiber, a hollow fiber, a nonwoven material, a woven fabric, a powder, a granulate, or of particles, and the carrier material is porous or nonporous.

8. The surface-functionalized carrier material according to claim 7, wherein the carrier material is present in the form of a membrane with a symmetric or asymmetric pore structure.

9. The surface-functionalized carrier material according to claim 7 or 8, wherein the porous carrier material has a pore size of 1 nm to 10 μm.

10. The surface-functionalized carrier material according to claim 1, wherein the alkyl groups of the radicals $R^1$, $R^3$, $R^4$ and $R^5$ and the acyl and the alkoxycarbonyl groups of $R^3$ are C1 to C20 alkyl units.

11. The surface-functionalized carrier material according to claim 1, wherein the aryl groups $R^1$, $R^3$, $R^4$ and $R^5$ and the aryloxycarbonyl group $R^3$ is a phenyl group.

12. A method for solid-phase synthesis of peptides or proteins, comprising the steps of:
    (a) providing a surface-functionalized carrier material according to any one of claims 1, 2, 3, 4, 5, 7, 8, 10 or 11, (b) covalently binding to the linker compound of said surface-functionalized carrier material a first amino acid, and (c) conducting a chain extension by successive coupling of additional amino acids to said first amino acid to produce said peptide or protein.

13. The method according to claim 12, wherein the linker compound contains a carboxyl group by $R^2$ being OH, and the first amino acid is bound to the linker compound by a peptide bond formed by reacting the amino group of the amino acid with the carboxyl group of the linker compound.

14. The method according to claim 13, wherein the linker compound contains an amino group by $R^3$ being H, and forming the peptide bond is controlled by blocking with a chemical protective group the carboxyl group of the amino acid or the amino group of the linker compound.

15. The method according to claim 12, wherein the linker compound contains an amino group by $R^3$ being H, and the first amino acid is bound to the linker compound by a peptide bond formed by reacting the carboxyl group of the amino acid with the amino group of the linker compound.

16. The method according to claim 15, wherein the linker compound contains a carboxyl group by $R^2$ being OH, and forming the peptide bond is controlled by blocking with a chemical protective group the amino group of the amino acid or the carboxyl group of the linker compound.

* * * * *